United States Patent [19]

Cozzi et al.

[11] Patent Number: 4,985,440
[45] Date of Patent: Jan. 15, 1991

[54] HYPOLIPIDAEMIC IMIDAZOL-2-YL-DERIVATIVES OF BICYCLIC COMPOUNDS

[75] Inventors: Paolo Cozzi; Germano Carganico; Dino Severino; Pierpaolo Lovisolo, all of Milan; Augusto Chiari, Florence, all of Italy

[73] Assignee: Farmitalia Carlo Erba, S.r.l., Milan, Italy

[21] Appl. No.: 435,429

[22] PCT Filed: Mar. 7, 1989

[86] PCT No.: PCT/EP89/00233
§ 371 Date: Dec. 19, 1989
§ 102(e) Date: Dec. 19, 1989

[87] PCT Pub. No.: WO89/08646
PCT Pub. Date: Sep. 21, 1989

[30] Foreign Application Priority Data

Mar. 9, 1988 [GB] United Kingdom ............... 8805628

[51] Int. Cl.$^5$ .............. A61K 31/415; C07D 403/00; C07D 233/54
[52] U.S. Cl. .................... 514/397; 514/400; 548/336; 548/346
[58] Field of Search ............ 548/336, 342, 346; 514/397, 400

[56] References Cited

FOREIGN PATENT DOCUMENTS 47-93909 4/1972 Japan.
2122997 1/1984 United Kingdom ............... 548/336
2145720A 8/1984 United Kingdom.

OTHER PUBLICATIONS

Cozzi et al., Il Farmaco, vol. 42, fasc 3, 1986.
Cozzi et al., J. Med. Chem., 1986, 29; 404-410.

Primary Examiner—Mary C. Lee
Assistant Examiner—Robert C. Whittenbaugh
Attorney, Agent, or Firm—Armstrong, Nikaido, Marmstein, Kubovcik & Murray

[57] ABSTRACT

Compounds having the following formula (I)

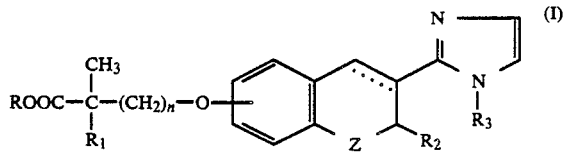

wherein
the symbol represents a single or double bond;
Z is —O— or —CH$_2$—;
n is zero, 1, 2 or 3;
each of R and R$_1$, independently, is hydrogen or C$_1$-C$_4$ alkyl;
each of R$_2$ and R$_3$, independently, is hydrogen or C$_1$-C$_8$ alkyl; and the pharmaceutically acceptable salts thereof;
are useful in therapy in particular as antidislipidaemic and antiatherosclerotic agents.

9 Claims, No Drawings

HYPOLIPIDAEMIC IMIDAZOL-2-YL-DERIVATIVES OF BICYCLIC COMPOUNDS

The present invention relates to new imidazol-2-yl-derivatives of bicyclic compounds, in particular to imidazol-2-yl-derivatives of 3,4-dihydro-2H-1-benzopyran, 2H-1-benzopyran, 1,2,3,4-tetrahydronaphthalene and 1,2-dihydronaphthalene, to a process for their preparation and to pharmaceutical compositions containing them.

The invention provides compounds having the following general formula (I)

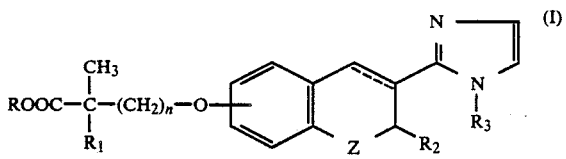

wherein
the symbol ==== represents a single or double bond;
z is —O— or —$CH_2$—;
n is zero, 1, 2 or 3;
each of R and $R_1$, independently, is hydrogen or $C_1$-$C_4$ alkyl;
each of $R_2$ and $R_3$, independently, is hydrogen or $C_1$-$C_8$ alkyl such as $C_1$-$C_6$ alkyl;
and the pharmaceutically acceptable salts thereof.

The invention also includes within its scope all the possible isomers, stereoisomers and their mixtures and the metabolites and the metabolic precursors or bioprecursors of the compounds of formula (I).

Pharmaceutically acceptable salts of the compounds of formula (I) include acid addition salts, with inorganic, e.g. nitric, hydrochloric, hydrobromic, sulphuric, perchloric and phosphoric, acids or organic, e.g. acetic, propionic, glycolic, lactic, oxalic, malonic, malic, maleic, tartaric, citric, benzoic, cinnamic, mandelic, fumaric, methanesulfonic and salicyclic acids, and salts with inorganic, e.g. alkali metal, especially sodium or potassium, bases or alkaline-earth metal, especially calcium or magnesium, or with organic bases, e.g. alkylamines, preferably triethylamine, or basic naturally occurring aminoacids, preferably arginine.

The alkyl groups may be branched or straight chain groups.

A $C_1$-$C_8$ alkyl group is e.g. a $C_1$-$C_6$ alkyl group such as a $C_1$-$C_3$ alkyl group. In particular it may be methyl, propyl, butyl or hexyl.

A $C_1$-$C_4$ alkyl group is preferably methyl, ethyl, propyl, isopropyl or butyl, in particular methyl or ethyl.

As stated above the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I) as defined above, wherein
the symbol ==== represents a double bond;
Z is —O— or —$CH_2$—;
n is zero or 3;
R is ethyl or isopropyl;
$R_1$ is methyl or ethyl;
$R_2$ is as defined above, for example hydrogen or $C_1$-$C_3$ alkyl;
$R_3$ is methyl; and the pharmaceutically acceptable salts thereof.

Specific examples of preferred compounds according to the present invention are:
ethyl 2-[3-(1-methyl-1H-imidazol-2-yl)-2H-1-benzopyran-6-yl]oxy-2-methylpropanoate;
ethyl 2-[2-methyl-3-(1-methyl-1H-imidazol-2-yl)-2H-1-benzopyran-6-yl]oxy-2-methylpropanoate;
ethyl 5-[3-(1-methyl-1H-imidazol-2-yl)-2H-1-benzopyran-6-yl]oxy-2,2-dimethylpentanoate;
ethyl 5-[2-methyl-3-(1-methyl-1H-imidazol-2-yl)-2H-1-benzopyran-6-yl]oxy-2,2-dimethylpentanoate;
ethyl 5-[3-(1-methyl-1H-imidazol-2-yl)-2-n-propyl-2H-1-benzopyran-6-yl]oxy-2,2-dimethylpentanoate;
ethyl 5-[3-(1-methyl-1H-imidazol-2-yl)-2-i-propyl-2H-1-benzopyran-6-yl]oxy-2,2-dimethylpentanoate;
ethyl 5-[2-n-butyl-3-(1-methyl-1H-imidazol-2-yl)-2H-1-benzopyran-6-yl]oxy-2,2-dimethylpentanoate;
ethyl 5-[2-n-hexyl-3-(1-methyl-1H-imidazol-2-yl)-2H-1-benzopyran-6-yl]oxy-2,2-dimethylpentanoate;
ethyl (±)-5-[3,4-dihydro-2,3-cis-3-(1-methyl-1H-imidazol-2-yl)-2-n-propyl-2H-1-benzopyran-6-yl]oxy-2,2-dimethylpentanoate;
ethyl 5-[5,6-dihydro-7-(1-methyl-1H-imidazol-2-yl)naphthalen-2-yl]oxy-2,2-dimethylpentanoate;
ethyl 5-[5,6-dihydro-6-methyl-7-(1-methyl-1H-imidazol-2-yl)naphthalen-2-yl]oxy-2,2-dimethylpentanoate;
ethyl 5-[5,6,7,8-tetrahydro-7-(1-methyl-1H-imidazol-2-yl)naphthalen-2-yl]oxy-2,2-dimethylpentanoate;
2-[3-(1-methyl-1H-imidazol-2-yl)-2H-1-benzopyran-6-yl]oxy-2-methylpropanoic acid;
5-[2-methyl-3-(1-methyl-1H-imidazol-2-yl)-2H-1-benzopyran-6-yl]oxy-2,2-dimethylpentanoic acid;
and the pharmaceutically acceptable salts thereof.

The compounds of the invention and the salts thereof can be obtained by a process comprising
(a) reacting a compound of formula (II)

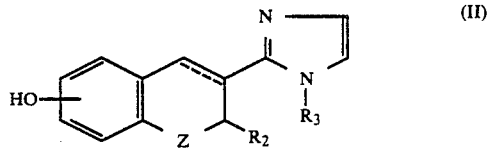

wherein the symbol====, Z, $R_2$ and $R_3$ are as defined above, with a compound of formula (III)

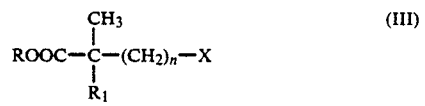

wherein X is an halogen atom or the residue of an active ester group and R, $R_1$ and n are as defined above; or
(b) reacting a compound of formula (II), as defined above, with acetone and chloroform, in the presence of an alkali metal hydroxide, so as to obtain a compound of formula (I) wherein n is zero, R is hydrogen, $R_1$ is methyl and the symbol====, Z, $R_2$ and $R_3$ are as defined above; and, if desired, converting a compound of formula (I) into another compound of formula (I), and/or, if desired, converting a compound of formula (I) into a salt thereof, and/or, if desired, converting a salt into a free compound, and/or, if desired, resolving a mixture of isomers of compounds of formula (I) into the single isomers.

When X, in a compound of formula (III), is an halogen atom it is e.g. chlorine or bromine. When X is the residue of an active ester, it is e.g. a mesyl or tosyl group, preferably a tosyl group. The reaction of a compound of formula (II) with a compound of formula (III) may be carried out according to well known methods in the presence of a suitable basic agent, in a suitable organic solvent; preferably with potassium tert. butoxide in tert.butanol or with anhydrous $K_2CO_3$ in acetone or with sodium hydride in dimethylformamide. The reaction may be performed at temperatures ranging from room temperature to reflux. Process variant (b) above may be carried out according to the well known Bargellini reaction [Gazz. Chim. Ital. 36, 344 (1906)]. The alkali metal hydroxide used in this reaction may be sodium or potassium hydroxide. In a preferred feature this process involves the reaction of a compound of formula (II) with powdered potassium hydroxide and chloroform in acetone. After the initial exothermicity of the reaction, the temperature is raised to reflux.

The optional conversion of a compound of formula (I) into another compound of formula (I) may be carried out by methods known in themselves.

Thus, for example, a compound of formula (I) containing an esterified carboxy group may be converted into a compound of formula (I) containing a free carboxy group, by acidic or alkaline hydrolysis, operating at temperatures ranging from room temperature to about 100° C. A compound of formula (I) containing a free carboxy group may be converted into a compound of formula (I) containing an esterified carboxy group by esterification, e.g. via the corresponding acid halide, e.g. chloride, or via a mixed anhydride, by reaction with an excess of a suitable $C_1$-$C_4$ alkyl alcohol, or by direct esterification, that is by reacting with the appropriate $C_1$-$C_4$ alcohol in the presence of an acidic catalyst, e.g. dry HCl or $BF_3$-etherate or $SOCl_2$.

A compound of formula (I) wherein the symbol ==== represents a double bond may be converted in a compound of formula (I) wherein the symbol ==== represents a single bond by reduction, preferably by catalytic hydrogenation in the presence of a suitable catalyst, e.g. palladium, platinum or $PtO_2$, in a suitable solvent, e.g. methanol or ethanol or acetic acid or n-hexane, operating at a pressure ranging from atmospheric pressure to about 30 atmospheres and at temperatures ranging from room temperature to about 100° C.

A compound of formula (I) wherein $R_3$ is hydrogen may be converted into another compound of formula (I) wherein $R_3$ is $C_1$-$C_6$ alkyl by well-known methods, for example by alkylating with a suitable $C_1$-$C_6$ alkyl halide, preferably chloride or bromide, in an organic solvent, e.g. dimethylformamide or dimethylsulfoxide, in the presence of a suitable basic agent, e.g. sodium hydride or an alkali metal hydroxide, a temperature ranging from about 0° C. to reflux.

The compounds of formula (II), in which the symbol ==== represents a double bond and Z, $R_2$ and $R_3$ are as defined above, may be obtained by β-elimination on a compound of formula (IV)

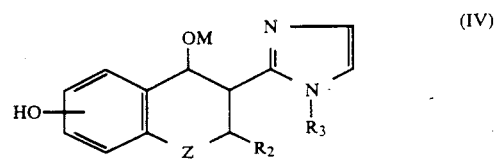

wherein Z, $R_2$ and $R_3$ are as defined above and M represents hydrogen or an acyl group, in particular an acetyl group. The reaction may be performed in the presence of a suitable solvent, such as, glacial acetic acid, mixtures of acetic anhydride-pyridine, dimethylformamide (DMF) or dimethylsulfoxide (DMSO), or benzene, in the presence of suitable amounts, even catalytic amounts, of a strong acid, e.g., concentrated $H_2SO_4$, HCl, or p-toluenesulphonic acid, at temperatures ranging from about 50° C. to the reflux temperature. The same conversion may also be performed by refluxing a compound of formula (IV) in concentrated acids, e.g. hydrochloric or hydrobromic acid. When in a compound of formula (IV) M is an acyl group, in particular, acetyl, the reaction may also be carried out by pyrolysis, at temperatures ranging, preferably, from about 200° C. to about 300° C.

The compounds of formula (II), in which the symbol ==== represents a single bond, may be obtained by reducing the corresponding compounds of formula (II), in which the symbol ==== represents a double bond, according to known methods. Such reduction, for instance, may be performed by following the same procedure described above for converting a compound of formula (I), in which the symbol ==== represents a double bond, into the corresponding compound of formula (I), in which the symbol ==== represents a single bond.

The compounds of formula (III) are known compounds.

The compounds of formula (IV) in which M represents hydrogen and Z, $R_2$ and $R_3$ are as defined above, may be obtained e.g. by reducing a compound of formula (V)

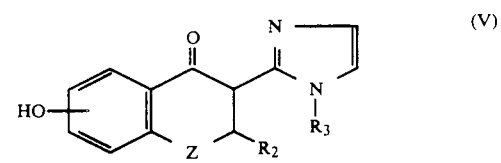

wherein Z, $R_2$ and $R_3$ are as defined above. The reduction may be performed according to well known procedures, for example, by treatment with an alkali metal borohydride, e.g. $NaBH_4$, in a suitable solvent, e.g. methyl or ethyl alcohol or a mixture of water and ethyl alcohol, or by treatment with $LiAlH_4$ in an anhydrous solvent, e.g. diethyl ether or tetrahydrofuran, at a temperature ranging, in both cases, preferably between 0° C. and the reflux temperature for reaction times varying approximately from 1 to 6 hours.

The compounds of formula (IV) wherein M is an acyl group may be obtained, for example, by reacting the corresponding compounds of formula (IV), in which M is hydrogen, with a suitable acyl halide, preferably chloride. The reaction with acetylchloride is, for example, performed in anhydrous pyridine or in an inert solvent, e.g. anhydrous benzene, if desired in the presence of an equimolar amount of a base such as triethylamine, at temperatures ranging from room temperature to about 60° C.

Compounds of formula (V) wherein Z is —CH$_2$— may preferably be obtained by ring closure in Friedel-Crafts conditions, e.g. in the presence of polyphosphoric acid, from the corresponding 2-(imidazol-2-yl)-4-phenylbutyric acids of formula (VI)

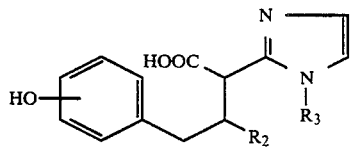

wherein R$_2$ and R$_3$ are as above defined.

Compounds (VI) may be obtained in turn from the corresponding nitriles (VII), preferably by alkaline hydrolysis, e.g. by treatment with potassium hydroxide in hydroalcoholic solution

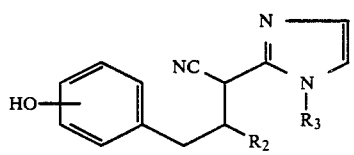

Nitriles (VII) may be obtained e.g. by reaction in the presence of a strong base like sodium hydride in a suitable solvent, e.g. DMF or DMSO, from the corresponding 2-cyanomethylimidazoles (VIII), which are known compounds, and the appropriate phenylethylhalides of formula (IX), which are known compounds or can be easily prepared by known methods.

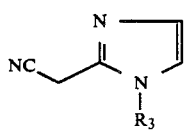

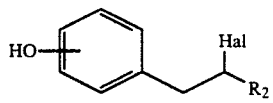

wherein Hal means halogen, e.g. chlorine or bromine, and R$_2$ and R$_3$ are as defined above.

The compounds of formula (V), wherein Z is O—, may be for example prepared by reacting a suitable acetylsalicyl chloride with a suitable 2-methylimidazole derivative according to known procedures, e.g. as described in J. Het. Chem. 23, 1693 (1986).

The compounds of the invention are useful as antidislipidaemic agents, indeed they show a high activity in lowering total serum cholesterol and particularly in lowering the cholesterol carried by the low density and the very low density lipoproteins (LDL and VLDL), as well as in increasing the ratio between high density lipoproteins (HDL) cholesterol and low and very low density lipoproteins (LDL-VLDL) cholesterol, and in lowering triglycerides. As known an elevated serum level of total cholesterol is a factor etiologically related to atherosclerosis and particularly to coronary heart disease (CHD) (see for example: Keys A, Seven countries: a multivariate analysis of death and CHD, Cambridge, Mass., Harvard University Press, 1980; Dawter T. R., The Framingham Study: the epidemiology of atherosclerotic disease, Cambridge Mass., Harvard University Press, 1980; Ross R., The pathology of atherosclerosis—an update, N. Engl. J. Med. (1986), 314, 488.

Moreover, elevated triglycerides levels are associated with an increased risk of CHD particularly in young subjects.

(See for example: Aberg A. et Al., Serum triglycerides are risk factors for myocardial infarction (MI) but not for angina pectoris: result from a 10-year follow-up of Uppsala Primary Prevention Study, Atherosclerosis (1985), 54, 89;

Carlson L. A. et Al., Risk factors for ischemic heart disease (IHD) in men and women: results of the 19-year follow-up of the Stockholm Prospective Study, Acta Med. Scand. (1985) 215, 207).

Finally a protective effect against CHD by elevated serum HDL has been observed in several epidemiological and clinical studies.

(See for example: Miller G. J. et Al., Plasma high density lipoprotein concentration and development of ischaemic heart disease, Lancet (1975), 1, 16;

Miller N. E. et Al., The Tromso Heart Study: high density lipoprotein and coronary heart disease: a prospective case-control study, Lancet (1977), 1, 965;

Gordon T. et Al., High density lipoprotein as a protective factor against coronary heart disease. Am. J. Med. (1977), 62, 707;

Castelli W. P. et Al. Incidence of coronary heart disease and lipoprotein cholesterol levels: the Framingham Study, JAMA (1986), 256, 2835).

On the other hand, clinical studies aimed at reducing elevated total cholesterol by pharmacological means have demonstrated a corresponding reduction of the incidence of CHD.

(See for example: Oliver M. F. et Al. A co-operative trial in the primary prevention of ischaemic heart disease using clofibrate: a report from the Committee of Principal Investigators, Br. Heart J. (1978), 40, 106.

Lipid Research Clinics Program. The LRC-CPPT results II. The relationship of reduction in incidence of CHD to cholesterol lowering, JAMA (1986), 251, 365).

Moreover a simultaneous increase in HDL cholesterol and reduction in non-HDL cholesterol, and hence increase of HDL/LDL-VLDL ratio significantly reduce the incidence of CHD.

(M. Heikki Frick et Al., Helsinki Heart Study: Primary Prevention Trial with Gemfibrozil in middle-aged men with dyslipidemia. N. Engl. J. Med. (1987), 317, 1237).

The activity of compounds of this invention was evaluated on Groups of Iva:SDIV (SPF) male rats fed standard diet (Altromin$^R$).

The compounds were suspended in "Methocel" (methyl cellulose, a 0.5% pseudosolution in water) and administered by stomach tube for 4 days.

Groups of animals were treated with the suspending agent only (control groups).

The total serum cholesterol was determined with the method of Allain C. C. (Clin. Chem. 20, 470, 1974).

The serum triglycerides were determined with the method of Spayd R. N. (Clin. Chem. 24, 1343, 1978).

The total serum HDL cholesterol was determined according to Demacker P. N. M. [Clin. Chem., 23, 1238 (1977)].

The following statistical methods were applied: the variance analysis Bartlett test [Properties of sufficiency and Statistical Tests-Proc. of the Royal Soc. of London A 160 (1937) pages 268–282] to prove the variance homogeneity and the Dunnett test [Dunnett C. W. - J. Amer. Stat. Ass., 50, 1096 (1955)].

Table 1 exemplifies the results obtained e.g. by testing the compounds of this invention, ethyl 5-[2-methyl-3-(1-methyl-1H-imidazol-2-yl)-2H-1-benzopyran-6yl]oxy-2,2-dimethylpentanoate (internal code FCE 25086), and ethyl 5-[5,6-dihydro-7-(1-methyl-1H-imidazol-2-yl)naphthalen-2-yl]oxy-2,2-dimethylpentanoate (internal code FCE 25390).

already demonstrated [Hudson H., Day A., Atherosclerosis (1982) 45, 109].

The dosage level suitable for oral administration to adult humans of the compounds of the invention, e.g. ethyl 5-[5,6-dihydro-7-(1-methyl-1H-imidazol-2-yl)naphthalen-2-yl]oxy-2,2-dimethylpentanoate, may range from about 100 mg to about 500 mg per dose 1 to 3 times a day, depending on the disease, age and weight of the patients involved.

The toxicity of the compounds of the invention is negligible, therefore they can be safely used in therapy. Nine hours food deprived mice and rats were treated orally with single administration of increasing doses,

TABLE 1

| Treatment | Dosage mg/kg/os | Activity as % variation vs. controls | | | |
|---|---|---|---|---|---|
| | | Tot. Chol. | LDL + VLDL Chol. | HDL/LDL + VLDL Chol. ratio | Triglycerides |
| FCE 25086 | 50 | −14** | −55** | +135** | −53** |
| FCE 25390 | 50 | −36** | −59** | +96** | −58** |
| Clofibrate | 50 | −11** | −19* | +18 | −22* |

*statistically significant $p \leq 0.05$
**statistically highly significant $p \leq 0.01$ Moreover the compounds of the invention show inhibitory activity of the enzyme acyl CoA: cholesterol acyltransfera se (ACAT-EC 2.3.1.26) which regulates the intracellular esterification of cholesterol (Suckling K. E., Stage E. F., J. Lip. Res. (1985) 26, 647) and thus the intracellular accumulation of cholesteryl esters.

The activity of this enzyme increases to the greatest extent during the atherosclerotic process in which the accumulation of esterified cholesterol in the atherosclerotic plaque is one of the predominant events (Brecher P., Chan C., B.B.A. (1980) 617, 458).

ACAT plays too a key role in the intestinal absorption of cholesterol and a significant activity of the enzyme has been observed in intestinal mucosa cells from several animal species (Heider J. G., Pickens C. E., Kelly L. A., J. Lip. Res. (1983) 24, 1127).

By virtue of their ACAT inhibitory activity the compounds of this invention, besides having antidislipidaemic activity, act also as direct antiatherosclerotic agents, able to inhibit the development of the atheromatous plaque, and therefore are useful in particular for the prevention of the coronary heart disease (CHD), e.g. myocardial infarction and angina.

The activity of the enzyme and its regulation by the compounds of the invention has been evaluated in our laboratories on microsomal preparations from atherosclerotic rabbit thoracic aorta (intimamedia) essentially according to F. P. Bell [Atherosclerosis (1981) 38, 81].

Table 2 exemplifies the results obtained by testing for instance a representative compound according to this invention: ethyl 5-[3-(1-methyl-1H-imidazol-2-yl)-2-n-propyl-2H-1-benzopyran-6-yl]oxy-2,2-dimethylpentanoate (internal code 25184)

TABLE 2

| IC$_{50}$ values for the ACAT inhibition in microsomes from atherosclerotic rabbit thoracic aortas. | | |
|---|---|---|
| Compound | IC$_{50}$M | limits $p = 0.95$ |
| FCE 25184 | $1.06 \times 10^{-6}$ | $0.77 \times 10^{-6} - 1.45 \times 10^{-6}$ |
| Bezafibrate | $5.13 \times 10^{-4}$ | $3.55 \times 10^{-4} - 8.29 \times 10^{-4}$ |

The values of IC$_{50}$ for the ACAT inhibition evidentiate that compound FCE 25184 is about 500 times more potent than Bezafibrate, a compound whose inhibitory activity in vitro (rabbit arterial microsomes) has been then housed and normally fed. The orientative acute toxicity (LD$_{50}$) was assessed on the seventh day after the treatment and resulted higher than 800 mg/kg.

The compounds of the invention can be administered in a variety of dosage forms, e.g. preferably orally, in the form of tablets, capsules, sugar, or film coated tablets, liquid solutions or suspensions.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions, and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The I.R. spectrum of the compounds was measured in solid phase (KBr) or Nujol solution or in a solution of a suitable solvent such as CHCl₃ using a Perkin-Elmer 125 spectro photometer.

The N.M.R. spectrum was measured preferably in solution of dimethylsulphoxide-d₆ or of CDCl₃, using a 90 M-Hertz Bruker HFX apparatus.

The $R_f$ values were determined by thin layer chromatography on ready-to-use silica gel plates of 0.25 mm coating thickness.

The following examples illustrate but do not limit the invention.

EXAMPLE 1

A mixture of 4.56 g (0.02 mol) of 3-(1-methyl-1H-imidazol-2-yl)-2H-1-benzopyran-6-ol [m.p. 210°–215° C., prepared following the procedure described in J. Heterocyclic Chem. 23, 1693 (1986)] and 2.3 g (0.02 mol) of potassium tert.butoxide in 100 ml of tert.butanol is heated, under vigorous stirring, at 50° C. for 30'. A solution of 3.9 g (0.02 mol) of ethyl bromoisobutyrate in 10 ml of tert.butanol is rapidly added dropwise and the resulting mixture refluxed for 4 hours. The solvent is evaporated under vacuum and the residue is taken up with H₂O (100 ml) and ethyl acetate. The aqueous solution is separated and extracted again with ethyl acetate (2×100 ml). The combined organic layers are washed with brine and dried over Na₂SO₄. After removal of the solvent under vacuum, the residue is chromatographed over silica gel (eluant chloroform/methanol 95/5) giving 4.7 g of ethyl 2-[3-(1-methyl-1H-imidazol-2-yl)-2H-1-benzopyran-6-yl]oxy-2-methylpropanoate, colourless oil.

Elemental analysis: Found: C 65.91; H 6.53; N 8.05. Calculated for C₁₉H₂₂N₂O₄: C 66.65; H 6.48; N 8.18.

T.L.C.: eluant AcOEt: n-Hexane=2:1, Rf=0.46.

N.M.R. (CDCl₃) δ p.p.m.: 1.27 (3H, t, C$\underline{H_3}$CH₂O), 1.54 (6H, s, (CH₃)₂C), 3.83 (3H, s, CH₃N), 4.26 (2H, q, CH₃C$\underline{H_2}$O), 5.18 (2H, d, O

CH₂C=), 6.60–6.80 (4H, m, phenyl+benzylic H), 6.91 (1H, d, imidazole), 7.08 (1H, d, imidazole).

By proceeding analogously, the following compounds can be prepared:
ethyl 2-[2-methyl-3-(1-methyl-1H-imidazol-2-yl)-2H-1-benzopyran-6-yl]oxy-2-methylpropanoate, oil.

Elemental analysis Found: C 66.98; H 6.79; N 7.63. Calculated for C₂₀H₂₄N₂O₄: C 67.39; H 6.78; N 7.86.

T.L.C.: eluant AcOEt: n-Hexane=2:1, Rf=0.44.

N.M.R. (CDCl₃) δ p.p.m.: 1.28 (3H, t, C$\underline{H_3}$CH₂OOC), 1.44 (3H, d, C$\underline{H_3}$CHO), 1.54 (6H, s, (CH₃)₂CO), 3.80 (3H, s, CH₃N), 4.25 (2H, q, CH₃C$\underline{H_2}$OOC), 5.58 (1H, q, CH₃C$\underline{H}$O), 6.60 (1H, s, CH benzylic), 6.70 (3H, m, phenyl) 6.90 (1H, d, imidazole), 7.08 (1H, d, imidazole).

EXAMPLE 2

Using the same procedure described in the Example 1, 2.28 g (0.01 mol) of 3-(1-methyl-1H-imidazol-2-yl)-2H-1-benzopyran-6-ol are reacted with 2.37 g (0.01 mol) of ethyl 5-bromo-2,2-dimethylpentanoate to give, after chromatographic purification on silica gel (eluant ethyl acetate/hexane, 1/1), 2.58 g of ethyl 5-[3-(1-methyl-1H-imidazol-2-yl)-2H-1-benzopyran-6-yl]oxy-2,2-dimethylpentanoate, m.p. 65°–68° C.

Elemental analysis Found: C 68.71; H 7.39; N 7.24. Calculated for C₂₂H₂₈N₂O₄: C 68.73; H 7.34; N 7.29.

T.L.C.: eluant AcOEt: n-Hexane=2:1, Rf=0.50.

N.M.R. (CDCl₃) p.p.m.: 1.21 (6H, s, (CH₃)₂C), 1.25 (3H, t, C$\underline{H_3}$CH₂O), 1.70 (4H, m, CH₂CH₂CH₂O), 3.85 (3H, s, C$\underline{H_3}$N), 3.90 (2H, m, CH₂CH₂C$\underline{H_2}$O), 4.13 (2H, q, CH₃C$\underline{H_2}$O), 5.17 (2H, d,

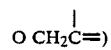
O CH₂C=)

6.60–6.80 (4H, m, phenyl+benzylic H), 6.91 (1H, d, imidazole), 7.08 (1H, d, imidazole).

By proceeding analogously, the following compounds can be prepared:
ethyl 5-[2-methyl-3-(1-methyl-1H-imidazol-2-yl)-2H-1-benzopyran-6-yl]oxy-2,2-dimethylpentanoate, oil.

Elemental analysis Found: C 69.05; H 7.57; N 6.97. Calculated for C₂₃H₃₀N₂O₄: C 69.32; H 7.58; N 7.02.

T.L.C.: eluant EtOAc: n-Hexane=4:6, Rf=0.33.

N.M.R. (DMSO-d₆) δ p.p.m.: 1.12 (6H, s, (CH₃)₂C), 1.14 (3H, t, C$\underline{H_3}$CH₂OOC), 1.27 (3H, d, C$\underline{H_3}$CHO), 1.60 (4H, m, CH₂C$\underline{H_2}$CH₂O), 3.90 (5H, m, CH₂CH₂C$\underline{H_2}$O+CH₃N), 4.05 (2H, q, CH₃C$\underline{H_2}$OOC), 5.50 (1H, q, CH₃C$\underline{H}$O), 6.90 (3H, m, phenyl), 7.26 (1H, s, CH benzylic), 7.66 (1H, d, imidazole), 7.74 (1H, d, imidazole), ethyl 5-[2-n-propyl-3-(1-methyl-1H-imidazol-2-yl)-2H-1-benzopyran-6-yl]oxy-2,2-dimethylpentanoate, oil.

Elemental analysis Found: C 69.89; H 7.96; N 6.51. Calculated for C₂₅H₃₄N₂O₄: C 70.39; H 8.03; N 6.56.

T.L.C.: eluant EtOAc: n-Hexane=1:1, Rf=0.43.

N.M.R. (CDCl₃) δ p.p.m.: 0.88 (3H, t, C$\underline{H_3}$CH₂CH₂), 1.21 (6H, s, (CH₃)₂C), 1.26 (3H, t, C$\underline{H_3}$CH₂OOC), 3.82 (3H, s, CH₃N), 3.90 (2H, m, CH₂C$\underline{H_2}$CH₂O), 4.13 (2H, q, CH₃C$\underline{H_2}$OOC), 5.41 (1H, dd, CH₂C$\underline{H}$O), 6.55–6.80 (4H, m, phenyl+benzylic H), 6.91 (1H, d, imidazole), 7.09 (1H, d, imidazole).

ethyl 5-[5,6-dihydro-7-(1-methyl-1H-imidazol-2-yl)-naphthalen-2-yl]oxy-2,2-dimethylpentanoate, oil Elemental analysis. Found: C 71.88; H 7.94; N 7.28. Calculated for C₂₃H₃₀N₂O₃: C 72.22; H 7.90; N7.32, T.L.C.: eluant AcOEt:n-Hexane=7:3, Rf=0.29, N.M.R. (CDCl₃) δ p.p.m.: 1.20 (6H, s, (CH₃)₂C), 1.24 (3H, t, C$\underline{H_3}$CH₂OOC), 1.50–1.80 (4H, m, CH₂CH₂CH₂O), 2.86 (4H, CH₂CH₂CH=), 3.80 (3H, s, C$\underline{H_3}$N), 3.92 (2H, m, CH₂C$\underline{H_2}$CH₂O), 4.11 (2H, q, CH₃C$\underline{H_2}$OOC), 6.60–7.07 (6H, m, phenyl+imidazole+benzylic H).

ethyl (±)-5-[3,4-dihydro-2,3-cis-3-(1-methyl-1H-imidazol-2-yl)-2-n-propyl-2H-1-benzopyran-6-yl]oxy-2,2-dimethylpentanoate, oil.

T.L.C.: eluant AcOEt: n-Hexane=1:1; Rf=0.22.
ethyl 5-[3-(1-methyl-1H-imidazol-2-yl)-2-i-propyl-2H-1-benzopyran-6-yl]oxy-2,2-dimethylpentanoate;
ethyl 5-[2-n-butyl-3-(1-methyl-1H-imidazol-2yl)-2H-1-benzopyran-6-yl]oxy-2,2-dimethylpentanoate;
ethyl 5-[2-n-hexyl-3-(1-methyl-1H-imidazol-2-yl)-2H-1-benzopyran-6-yl]oxy-2,2-dimethylpentanoate, and
ethyl 5-[5,6-dihydro-6-methyl-7-(1-methyl-1H-imidazol-2-yl)-naphthalen-2-yl]oxy-2,2-dimethylpentanoate.

EXAMPLE 3

Finely powdered potassium hydroxide (25 g, 0.445 mol) is added to a solution of 12.75 g (0.037 mol) of 3-(1-methyl-1H-imidazol-2-yl)-2H-1-benzopyran-6-ol in 90 ml (1.22 mol) of acetone. Chloroform (10.5 ml, 0.13 mol) is added dropwise and the mixture heated, under stirring, at 35° C. for 1 hour. After refluxing for an additional hour, the reaction mixture is cooled to room temperature and poured into ice-water (150 ml). The solution is acidified until pH 6 with 1N HCl and the precipitate is filtered, washed with ether and dried under vacuum at 0° C. The crude product is chromatographed on silica gel (eluant giving 13.15 g of 2-[3-(1-methyl-1H-imidazol-2-yl)-2H-1-benzopyran-6-yl]oxy-2-methylpropanoic acid, m.p. 187°-190° C.

Elemental analysis Found: C 65.11; H 5.80; N 8.88, Calculated for $C_{17}H_{18}N_2O_4$: C 64.95; H 5.77; N 8.91, T.L.C.: eluant $CHCl_3:CH_3OH:CH_3COOH = 170:30:1$, N.M.R. (DMSO-$d_6$) δ p.p.m.: 1.46 (6H, s, $(CH_3)_2C$), 2.83 (3H, s, $CH_3N$), 5.06 (2H, d, $OCH_2$), 6.65–6.80 (3H, m, phenyl), 6.93 (1H, m, benzylic H), 6.95 (1H, d, imidazole), 7.25 (1H, d, imidazole).

EXAMPLE 4

A solution of 0.82 g (0.0018 mol) of ethyl 5-[3-(1-methyl-1H-imidazol-2-yl)-2-n-propyl-2H-1-benzopyran-6-yl]oxy-2,2-dimethylpentanoate in absolute ethanol (100 ml) is hydrogenated in the presence of 250 mg of 10% Pd on activated carbon at 3.42 atm. for 4 hours.

The catalyst is filtered off and the solvent is removed under vacuum. The residue is chromatographed on silica gel (eluant chloroform/methanol, 9/1), giving 0.71 g of ethyl (±)-5-[3,4-dihydro-2,3-cis-3-(1-methyl-1H-imidazol-2-yl)-2-n-propyl-2H-1-benzopyran-6-yl]oxy-2,2-dimethylpentanoate, oil.

Elemental analysis: Found: C 69.83; H 8.45; N 6.49, Calculated for $C_{25}H_{36}N_2O_4$: C 70.06; H 8.46; N 6.53, T.L.C.: eluant AcOEt: n-Hexane = 1:1, Rf = 0.22

N.M.R. (DMSO-$d_6$) δp.p.m.: 0.73 (3H, t, $CH_3CH_2CH_2$), 1.14 (6H, s, $(CH_3)_2C$), 1.17 (3H, t, COO$CH_2CH_3$), 1.10–1.65 (8H, m, four $CH_2$) 3.12–3.36 (2H, ddd, $CH$benzylic), 3.86 (2H, m, $OCH_2$), 3.89 (3H, s, $NCH_3$), 3.99 (1H, m,

CH$_2$CHCHO)

4.04 (2H, q, COO$CH_2CH_3$), 4.48 (1H, m, $OCH$—), 6.50–7.69 (5H, m, phenyl + imidazole).

By proceeding analogously, the following compound can be prepared:
ethyl 5-[5,6,7,8-tetrahydro-7-(1-methyl-1H-imidazol-2-yl) naphthalen-2-yl]oxy-2,2-dimethylpentanoate.

EXAMPLE 5

A solution of 1 g (2.23 mmol) of ethyl 5-[2-methyl-3-(1-methyl-1H-imidazol-2-yl)-2H-1-benzopyran-6-yl]oxy-2,2-dimethylpentanoate in 0.5 N methanolic potassium hydroxide solution is refluxed for 6 hours.

The solvent is evaporated under vacuum and the residue taken up with water (100 ml). The aqueous solution is washed with ethyl acetate (2 × 50 ml) and the pH is adjusted at about 6 with 1N HCl. The precipitate is filtered, washed with ether and dried under vacuum at 100° C., giving 0.74 g of 5-[2-methyl-3-(1-methyl-1H-imidazol-2-yl)-2H-1-benzopyran-6-yl]oxy-2,2-dimethylpentanoic acid, m.p. 145°-146° C.

Elemental analysis Found: C 68.01; H 7.10; N 7.45, Calculated for $C_{21}H_{26}N_2O_4$: C 68.08; H 7.07; N 7.56, T.L.C.: eluant $CHCl_3$: $CH_3OH = 95:5$, Rf = 0.50

N.M.R. (DMSO-$d_6$) δ p.p.m.: 1.09 (6H, s, $(CH_3)_2C$), 1.27 (3H, d, OCH $CH_3$), 1.58 (4H, m, $CH_2CH_2CH_2O$), 3.81 (3H, s, $CH_3N$), 3.88 (2H, m, $CH_2CH_2CH_2O$), 5.48 (1H, q, O$CH$ $CH_3$), 6.70–7.30 (6H, m, phenyl + imidazole + benzylic H).

EXAMPLE 6

A mixture of 4 g (0.013 mol) of 2-[3-(1-methyl-1H-imidazol-2-yl)-2H-1-benzopyran-6-yl]oxy-2-methylpropanoic acid and 50 ml of $SOCl_2$ is refluxed for 4 hours. The excess of $SOCl_2$ is evaporated under vacuum. The residue is treated with absolute ethanol and refluxed for 5 hours. The organic solvent is removed under reduced pressure. Water (100 ml) is added and the pH adjusted to neutrality. Extraction with EtOAc (3 × 80 ml), washing with brine and drying over $Na_2SO_4$ gives, after removal of the solvent, a crude product that is chromatographed on silica gel (eluant ethyl acetate/hexane, 1/1), furnishing 3.82 g of ethyl 2-[3-(1-methyl-1H-imidazol-2-yl)-2H-1-benzopyran-6-yl]oxy-2-methylpropanoate.

EXAMPLE 7

A solution of 2 g (5.3 mmol) of ethyl 2-[3-(1-methyl-1H-imidazol-2-yl)-2H-1-benzopyran-6-yl]oxy-2-methylpropanoate in 30 ml of absolute ethanol is treated with gaseous HCl for 15 min, with external cooling. The solution is treated, under vigorous stirring, with 100 ml of ether. The precipitate is filtered, washed with ether and dried under vacuum, giving 1.95 g of ethyl 2-[3-(1-methyl-1H-imidazol-2-yl)-2H-1-benzopyran-6-yl]oxy-2-methylpropanoate hydrochloride, m.p. 154°-156° C.

Elemental analysis: Found: C 59.80; H 6.15; N 7.31; Cl 9.36, Calculated for $C_{19}H_{23}ClN_2O_4$: C 60.24; H 6.12; N 7.39; Cl 9.36, By proceeding analogously, the following compounds can be prepared:
ethyl 2-[2-methyl-3-(1-methyl-1H-imidazol-2-yl)-2H-1-benzopyran-6-yl]oxy-2-methylpropanoate hydrochloride, m.p. 160°-165° C.;
ethyl 5-[2-methyl-3-(1-methyl-1H-imidazol-2-yl)-2H-1-benzopyran-6-yl]oxy-2,2-dimethylpentanoate hydrochloride, m.p. 135°-138° C.;
ethyl 5-[3-(1-methyl-1H-imidazol-2-yl)-2-n-propyl-2H-1-benzopyran-6-yl]oxy-2,2-dimethylpentanoate hydrochloride, m.p. 65°-70° C.;
ethyl 5-[5,6-dihydro-7-(1-methyl-1H-imidazol-2-yl)-naphthalen-2-yl]oxy-2,2-dimethylpentanoate hydrochloride, m.p. 158°-160° C.
ethyl (±)-5-[3,4-dihydro-2,3-cis-3-(1-methyl-1H-imidazol-2-yl)-2-n-propyl-2H-1-benzopyran-6-yl]oxy-2,2-dimethylpentanoate hydrochloride, m.p. 100°-105° C.

EXAMPLE 8

With the usual methods of pharmaceutical technique, preparation can be made of capsules having the following composition:

| Composition: | |
| --- | --- |
| Ethyl 5-[5,6-dihydro-7-(1-methyl-1H-imidazol-2-yl)-naphthalen-2-yl]oxy-2,2-dimethylpentanoate | 200 mg |
| Starch | 8 mg |
| Microcrystalline cellulose | 23 mg |
| Talc | 8 mg |
| Magnesium stearate | 5 mg |

We claim:
1. A compound having the following formula (I)

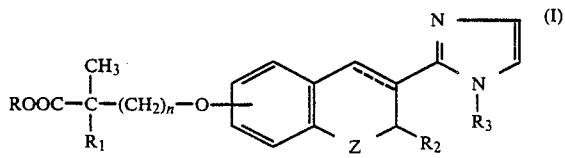

wherein
the symbol ===== represents a single or double bond;
Z is —O— or —CH$_2$—;
n is zero, 1, 2 or 3;
each of R and R$_1$, independently, is hydrogen or C$_1$–C$_4$ alkyl;
each of R$_2$ and R$_3$, independently, is hydrogen or C$_1$–C$_8$ alkyl; or a pharmaceutically acceptable salt thereof.

2. A compound of formula (I), according to claim 1, wherein each of R$_2$ and R$_3$, independently, is hydrogen or C$_1$–C$_6$ alkyl; or a pharmaceutically acceptable salt thereof.

3. A compound of formula (I), according to claim 1, wherein the symbol ===== represents a double bond;
Z is —O— or —CH$_2$—;
n is zero or 3;
R is ethyl or isopropyl;
R$_1$ is methyl or ethyl;
R$_2$ is as defined in claim 1;
R$_3$ is methyl; or a pharmaceutically acceptable salt thereof.

4. A compound of formula (I), according to claim 3, wherein R$_2$ is hydrogen or C$_1$–C$_3$ alkyl; or a pharmaceutically acceptable salt thereof.

5. A compound of formula (I), according to claim 1, selected from the group consisting of:
ethyl 2-[3-(1-methyl-1H-imidazol-2-yl)-2H-1-benzopyran-6-yl]oxy-2-methylpropanoate;
ethyl 2-[2-methyl-3-(1-methyl-1H-imidazol-2-yl)-2H-1-benzopyran-6-yl]oxy-2-methylpropanoate;
ethyl 5-[3-(1-methyl-1H-imidazol-2-yl)-2H-1-benzopyran-6-yl]oxy-2,2-dimethylpentanoate;
ethyl 5-[2-methyl-3-(1-methyl-1H-imidazol-2-yl)-2H-1-benzopyran-6-yl]oxy-2,2-dimethylpentanoate;
ethyl 5-[3-(1-methyl-1H-imidazol-2-yl)-2-n-propyl-2H-1-benzopyran-6-yl]oxy-2,2-dimethylpentanoate;
ethyl 5-[3-(1-methyl-1H-imidazol-2-yl)-2-i-propyl-2H-1-benzopyran-6-yl]oxy-2,2-dimethylpentanoate;
ethyl 5-[2-n-butyl-3-(1-methyl-1H-imidazol-2-yl)-2H-1-benzopyran-6-yl]oxy-2,2-dimethylpentanoate;
ethyl 5-[2-n-hexyl-3-(1-methyl-1H-imidazol-2-yl)-2H-1-benzopyran-6-yl]oxy-2,2-dimethylpentanoate;
ethyl (±)-5-[3,4-dihydro-2,3-cis-3-(1-methyl-1H-imidazol-2-yl)-2-n-propyl-2H-1-benzopyran-6-yl]oxy-2,2-dimethylpentanoate;
ethyl 5-[5,6-dihydro-7-(1-methyl-1H-imidazol-2-yl)-naphthalen-2-yl]oxy-2,2-dimethylpentanoate;
ethyl 5-[5,6-dihydro-6-methyl-7-(1-methyl-1H-imidazol-2-yl)naphthalen-2-yl]oxy-2,2-dimethylpentanoate;
ethyl 5-[5,6,7,8-tetrahydro-7-(1-methyl-1H-imidazol-2-yl)naphthalen-2-yl]oxy-2,2-dimethylpentanoate;
2-[3-(1-methyl-1H-imidazol-2-yl)-2H-1-benzopyran-6-yl]oxy-2-methylpropanoic acid;
5-[2-methyl-3-(1-methyl-1H-imidazol-2-yl)-2H-1-benzopyran-6-yl]oxy-2,2-dimethylpentanoic acid;
and the pharmaceutically acceptable salts thereof.

6. A pharmaceutical composition containing a suitable carrier and/or diluent and, as an active principle, an effective amount of a compound of formula (I) according to claim 1 or a pharmaceutically acceptable salt thereof.

7. A method of treating a host suffering from dislipidaemia comprising administering thereto an effective amount of a compound of claim 1.

8. A method of treating a host suffering from atherosclerosis comprising administering thereto an effective amount of a compound of claim 1.

9. A method of preventing coronary heart disease in a host comprising administering thereto an effective amount of a compound of claim 1.

* * * * *